United States Patent [19]

Johnson et al.

[11] 4,042,462
[45] Aug. 16, 1977

[54] CREATINE PHOSPHOKINASE DETERMINATION METHOD

[75] Inventors: John H. Johnson, Kirkwood; Lloyd E. Weeks, St. Louis, both of Mo.

[73] Assignee: Monsanto Company, St. Louis, Mo.

[21] Appl. No.: 644,203

[22] Filed: Dec. 24, 1975

[51] Int. Cl.² ............................................. G01N 31/14
[52] U.S. Cl. ............................................. 195/103.5 R
[58] Field of Search ................ 195/103.5 R; 204/1 E, 204/195 B

[56] References Cited

U.S. PATENT DOCUMENTS

| | | | |
|---|---|---|---|
| 3,403,077 | 9/1968 | Berger et al. | 195/103.5 R |
| 3,540,984 | 11/1970 | Deutsch | 195/103.5 R |
| 3,929,580 | 12/1975 | Forgione et al. | 195/103.5 R |

OTHER PUBLICATIONS

Rosalki "An Improved Procedure for Serum Creative Phosphakinase Determination", J. Lab. & Clin. Med. 69 (1967), pp. 696-705.

Greenbaum et al "The Estimation of the Oxidized and Reduced Forms of the Nicotinamide Nucleotides" Biochem. J. 95, (1965) pp. 161-166.

*Primary Examiner*—Alvin E. Tanenholtz
*Assistant Examiner*—C. A. Fan
*Attorney, Agent, or Firm*—Scott J. Meyer; John D. Upham

[57] ABSTRACT

A method of determining creatine phosphokinase activity in biological fluids comprising reacting a biological fluid sample with a coupled enzyme series in an oxygenated aqueous solution containing creatine phosphate, ADP, glucose, HK, G-6-PDH, NADP and an electron transfer agent and measuring the uptake of oxygen by the oxidation of the resulting NADPH with an oxygen-sensing electrode.

8 Claims, No Drawings

CREATINE PHOSPHOKINASE DETERMINATION METHOD

BACKGROUND OF THE INVENTION

This invention relates to a method for the determination of creatine phosphokinase.

Creatine phosphokinase (CPK) is a kinase enzyme which catalyzes the reversible transfer of a phosphate group from creatine phosphate to adensoine-5'-diphosphate (ADP) according to the following equation:

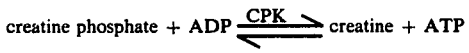

CPK activity is greatest in striated muscle tissue, brain and heart tissue. Serum CPK activity is elevated in all types of muscular dystrophy and becomes elevated within a few hours after a myocardial infarction. Consequently, tests for CPK activity levels are of significant clinical interest.

Various methods have been developed heretofore for the assay of CPK, including colorimetric, fluorimetric, and coupled enzymatic methods.

In one typical coupled enzyme system, the reaction of creatine and ATP is initially catalyzed by CPK to form creatine phosphate and ADP. This reaction is then coupled to two other enzyme reactions which employ phosphoenolpyruvate, reduced nicotinamide adenine dinucleotide (NADH) and the enzymes pyruvic kinase and lactate dehydrogenase. These reactions lead ultimately to the oxidation of NADH which is followed spectrophotometrically at 340 nm. This method was developed essentially by Tanzer and Gilvarg, *J. Biol. Chem.* 234, 3201-4 (1959), and modifications are described in U.S. Pat. No. 3,403,077.

Another coupled enzyme method is based on the reverse reaction in which creatine phosphate and ADP substrates react in the presence of CPK to form creatine and ATP. The ATP generated serves in an auxiliary reaction to phosphorylate glucose in the presence of hexokinase (HK). The resulting glucose-6-phosphate (G-6-P) then becomes a substrate for the ultimate indicator reaction which is catalyzed by glucose-6-phosphodehydrogenase (G-6-PDH) in the presence of nicotinamide adenine dinucleotide phosphate (NADP) to form 6-phosphogluconate and reduced nicotinamide adenine dinucleotide phosphate (NADPH). The production of NADPH is followed spectrophotometrically at 340 nm. This coupled enzyme system can be shown by the following series of equations:

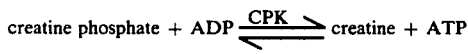
(1)

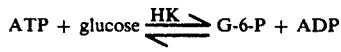
(2)

(3)

The latter coupled enzyme system, first described by Nielsen and Ludvigsen and by Oliver, has been amplified by Rosalki, *J. Lab. Clin. Med.* 69, 696–705 (1967), and further modifications are disclosed in U.S. Pat. Nos. 3,413,198, 3,485,724 and 3,540,984.

While the foregoing spectrophotometric methods are useful, they have the disadvantage in that each individual serum sample assay takes at least about 8 to 15 minutes to complete.

BRIEF SUMMARY OF THE INVENTION

In accordance with the present invention, CPK activity in biological fluids is determined by a coupled enzyme system which first employs creatine phosphate, ADP and the HK and G-6-PDH auxiliary reactions described above. The resulting NADPH is then oxidized in the presence of an electron transfer agent and the uptake of dissolved oxygen is determined with an oxygen-sensing electrode. This method advantageously can be carried out rapidly in about three minutes or less per sample assay.

DETAILED DESCRIPTION OF THE INVENTION

In general, the coupled enzyme system of this invention proceeds initially according to the reaction sequence described above which leads to the production of NADPH. Instead of stopping at this point, the reaction sequence then continues further to the oxidation of NADPH as follows:

The uptake of oxygen in the latter reaction is determined by an oxygen-sensing electrode and the rate of change in the electrode output is proportional to the CPK activity in the biological sample being tested.

All of the chemical components required in the foregoing reactions are well-known and available commercially. Thus, the ADP and NADP compounds can be obtained from mammalian muscle tissue and are generally available commercially as water soluble salts, usually as the sodium salts.

Creatine phosphate also is available from mammalian muscle tissue while glucose is generally obtained commercially by the hydrolysis of cornstarch.

The HK and G-6-PDH enzymes can be obtained from yeasts and other microorganisms as seen, for example, from U.S. Pat. No. 3,794,562. The HK enzyme has an absolute cofactor requirement for $Mg^{++}$ ion for activity and this can be supplied by the addition of a small but effective amount of a water-soluble magnesium salt, for example, magnesium sulfate or magnesium acetate, to the reaction medium.

The CPK enzyme is known to be relatively unstable in blood serum samples. Its activity can usually be restored and maintained by the addition of a small but activating amount of a sulfhydryl (thiol) compound such as, for example, $\beta$-mercaptoethanol, cysteine, acetyl cysteine and glutathione as described in U.S. Pat. No. 3,403,077, or dithiothreitol as disclosed in U.S. Pat. No. 3,540,984. However, in the present invention, cysteine and glutathione have been found to interfere with the electron transfer agent to give false positives in the assay. On the other hand, dithiothreitol has been found to be useful without causing such interference in the assay. Use of from about 0.5 to about 2 millimolar concentration of dithiothreitol is preferred. Amounts substantially in excess of this level cause crosslinking and eventual solidification of the serum sample.

The enzyme myokinase, which is another component present in serum and also appears as a contaminant in some HK preparations, tends to compete for the ATP required to phosphorylate glucose by HK. Inhibition of myokinase can be achieved by the addition of a small but inhibitory amount of adenosine-5'-monophosphate (AMP) to the reaction medium. Use of from about $1 \times 10^{-3}$ to about $8.75 \times 10^{-3}$ moles of AMP is preferred. Amounts substantially in excess of this level do not significantly increase inhibition beyond the 85–90% level that is typical with commercially available spectrophotometric assay methods.

In general, molar equivalent amounts of ADP, NADP, creatine phosphate and glucose and small but catalytically effective amounts of the enzymes are employed in the coupled enzyme reactions of this invention. However, an excess of the HK and G-6-PDH enzymes are preferred to assure that these enzymes do not become the limiting factors in the overall reaction. Use of from about 2 to about 10 International Units (I.U.) of HK and from about 2 to about 10 I.U. of G-6-PDH per sample assay are preferred.

The oxidation reaction in which the reduced form of the coenzyme, NADPH, is converted to the oxidized form, NADP, requires the presence of an electron transfer agent or electron acceptor. Useful electron transfer agents include, for example, diaphorase from pig heart or Clostridium as described in U.S. Pat. No. 3,791,931. Diaphorase from these sources has been found to be suitable at a level of about 1.5 mg per test. Another suitable electron transfer agent is phenazine methosulfate. This compound has been found to be suitable at levels ranging from about $2.6 \times 10^{-4}$ molar to about $6.5 \times 10^{-6}$ molar and a level of about $1.39 \times 10^{-4}$ molar is optimal. Use of the phenazine methosulfate electron transfer agent in the estimation of the oxidized and reduced forms of nicotinamide nucleotides with an oxygen-sensing electrode is described by Greenbaum et al., *Biochem. J.* 95, 161–6 (1965).

The reagents which comprise the coupled enzyme system preferably are prepared in an aqueous buffered medium having a pH of from about 6 to about 7 and preferably pH of about 6.8. Suitable buffers for this purpose are, for example, glycine and tris[tris(hydroxymethyl) aminomethane].

Incubation time and temperature conditions are not critical and can be varied to facilitate completion of the reactions. Usually, the end point is reached within about 3 minutes or less at incubation temperatures ranging from about 25° to 40° C.

The coupled enzyme reaction series is conveniently carried out in a cuvette or other such sample container with an attached oxygen electrode. An attached recorder for the electrode indicates the electrode output. The reaction equilibrium point at which the reaction reaches a maximum as indicated by the output in millivolts on the recorder trace is taken as the end point for the determination.

In general, the oxygen-sensing electrode employed in this invention comprises an anode, a cathode, an electrolyte solution and means whereby the diffusion flow of oxygen through a semi-permeable membrane into the electrolyte is measured. The current output is a linear function of oxygen tension which in turn varies directly with the diffusion flow of oxygen.

Oxygen-sensing electrodes are well-known. The Clark pO$_2$ electrode described in U.S. Pat. No. 2,913,386 is typical. In this electrode, oxygen diffuses through a gas-permeable polymeric membrane and is reduced at a platinum cathode which is kept at a fixed potential with respect to a silver-silver chloride reference anode. Such electrodes have been used heretofore for the determination of blood glucose levels by measuring the oxygen uptake in a glucose oxidase enzyme catalyzed reaction. Illustrative of such use of the Clark pO$_2$ electrode are the report by Kunz and Stastny, *Clin. Chem.* 20, 1018–22 (1974) and the review article by Gough and Andrade, *Science,* 180, 380–84 (1973).

Oxygen-sensing electrodes also are commercially available or can be prepared in the laboratory. One such suitable electrode, commercially available from Beckman Instruments, Inc., consists of a gold cathode which is separated by an epoxy coating from a tubular silver anode. An inner sensor body is housed in a plastic casing and comes into contact with the sample reagent solution only through a Teflon (duPont polytetrafluoroethylene) plastic membrane. As oxygen diffuses through this membrane, it is electrochemically reduced at the cathode by an applied potential of 0.8 volts. The reaction causes a current to flow between the anode and cathode which is proportional to the partial pressure of oxygen in the reagent sample.

An example of a suitable laboratory prepared oxygen-sensing electrode for measuring dissolved oxygen in solution is described by Johnson et al., *Biotechnol. & Bioeng.* 6, 457–68 (1964). This electrode has a silver cathode, a lead anode, an acetate buffer as an electrolyte, and a Teflon plastic membrane. The electrolyte is an aqueous solution containing 0.1 molar sodium acetate and 0.1 molar acetic acid, or a more concentrated solution containing 5 M acetic acid and 0.5 M sodium acetate. A modification of this electrode is described by Borkowski and Johnson, *Biotechnol. & Bioeng.* 9, 635–39 (1967), in which the electrolyte is an aqueous solution of 5 M acetic acid, 0.5 M sodium acetate, 0.1 M lead acetate and has a pH of about 3. In addition, a silicone rubber insulated filter of glass wool or nylon is inserted between the lead anode and silver cathode to prevent lead particles from dropping onto the silver cathode and eventually causing a short circuit. The electrode has a linear response from below 0.00002 to over 0.2 atmosphere of oxygen. In this electrode, the reaction at the silver cathode is believed to be $$\tfrac{1}{2} O_2 + H_2O + 2e^- \rightarrow 2OH^-$$

while at the lead anode the loss of electrons produces lead ions.

$$Pb \rightarrow Pb^{++} + 2e^-$$

The lead ions combine with the hydroxyl to form lead hydroxide on the anode surface to result in an overall reaction as follows:

$$\tfrac{1}{2} O_2 + Pb + H_2O \rightarrow Pb(OH)_2$$

With acetate as the electrolyte, a deposit of basic lead acetate builds up on the lead surface and lead salts accumulate in the electrolyte. The expendable materials thereby are the lead anode and the acetate of the electrolyte.

A further modification of the above-described Johnson electrode is disclosed by Elsworth, *The Chemical Engineer,* February 1972, pp. 63–71.

Still other oxygen-sensing electrodes for use in the present invention are described in U.S. Pat. Nos. 3,449,231, 3,454,485 and 3,539,455.

Although Teflon plastic and silicone rubber have been specifically described above, it should be understood that other membrane materials permeable to oxygen and impermeable to water and electrolytes can be used in the oxygen-sensing electrode, for example, polyethylene, polypropylene, polystyrene and polyvinyl chloride. Other suitable anode-cathode materials include, for example, any noble metal cathode such as gold, silver or rhodium in conjunction with a zinc, cadmium or lead anode.

In the instant invention, the diffusion flow of oxygen through the plastic membrane is reduced by the presence of CPK in the coupled enzyme catalyzed reaction as defined hereinbefore.

The following detailed examples will further illustrate the invention although it should be understood that the invention is not limited to these specific examples.

EXAMPLE 1

Four bovine serum samples, 50 microliters ($\mu$l) each, were spiked with, respectively, 50, 110, 165, and 220 International Units (I.U.) of CPK to thereby serve as test serum samples.

Reagents for the coupled enzyme series of reactions were prepared in aqueous solution as follows:

| Enzyme/Coenzyme Reagent Mix | |
|---|---|
| ADP | $8.95 \times 10^{-6}$ molar |
| NADP | $7.1 \times 10^{-4}$ molar |
| Creatine phosphate | $1.08 \times 10^{-2}$ molar |
| HK | 5.4 I.U./test sample |
| G-6-PDH | 4.8 I.U./test sample |

| Buffer Solution |
|---|
| tris buffer, pH 6 |
| 0.03 Molar $Mg(C_2H_3O_2)_2$ |
| 0.02 Molar glucose |

The buffer solution was deaerated under vacuum and then reaerated to saturation while stirring at 37° C for 30 minutes. One ml of the buffer solution was then transferred to a cuvette with an attached oxygen-sensing electrode while stirring at 500 rpm. This was followed by the addition of 100 $\mu$l of the enzyme/coenzyme reagent mix, held at 37° C, 50 $\mu$l of phenazine methosulfate (one mg./ml.) and a 50 $\mu$l serum sample spiked with CPK. To this was added 2 millimolar dithiothreitol and $8.75 \times 10^{-3}$ molar AMP. The maximum rate of decrease in electrode output in millivolts/minute was determined from the recorder trace. This decrease occurred within about 1 to 2 minutes following an initial 45 to 60 second lag. The relationship of CPK activity in the serum samples vs. mv/min electrode output was found to be substantially linear.

The oxygen sensing electrode employed in this example was a modification of the membrane electrode described by Elsworth, *The Chemical Engineer*, February 1972, pp. 63–71. This modification employed a silver cathode and a lead anode. The electrolyte, which consisted of 5.0M acetic acid, 0.5M sodium acetate and 0.1M lead acetate, instead of being used in a liquid phase as described by Elsworth, was employed in a gelled form by the addition of a small amount of Syton (Monsanto silica gel) and then applied in film form covered by a Teflon plastic film.

The electrode was attached to a cuvette, which had an inner Teflon plastic sleeve lining, by entry from the side of the cuvette. The reagents were introduced into the cuvette by entry from the open top. An agitated water bath assembly was employed to maintain a stirring speed of about 300 rpm and a temperature of about 37° C for the reaction components. A Beckman recorder attached to the electrode terminals indicated the electrode output.

Replicated CPK assays were carried out with High Control Serum (Environmental Services, Inc., Dublin, Ohio) using 50 samples each with the above oxygen-sensing electrode method, with the spectrophotometric method of Rosalki, supra, and with a commercially available CPK assay kit (Calbiochem). The oxygen-sensing electrode method of this invention showed a coefficient of variation (CV) of 5.0%, which compared favorably with the Rosalki method which showed a CV of 10.5% and the commercial CPK kit which showed a CV of 7.3%.

EXAMPLE 2

Example 1 is repeated except that diaphorase in the amount of 30 mg/ml. is used in place of the phenazine methosulfate with substantially similar results.

Various other examples will be apparent to the person skilled in the art after reading the foregoing disclosure without departing from the spirit and scope of the invention and it is intended that all such examples be included within the scope of the appended claims.

What is claimed is:

1. The method of determining creatine phosphokinase in blood serum or plasma comprising reacting a sample of said blood serum or plasma with an oxygenated aqueous solution containing creatine phosphate, ADP, glucose, HK, G-6-PDH, NADP and diaphorase or phenazine methosulfate electron acceptor at a temperature of from about 25° to about 40° C and a pH of from about 6 to about 7 and measuring the uptake of oxygen by the oxidation of the resulting NADPH with an oxygen sensing electrode.

2. The method of claim 1 in which the pH is maintained by a buffer selected from the group consisting of tris buffer and glycine buffer.

3. The method of claim 1 in which the electron acceptor is phenazine methosulfate.

4. The method of claim 1 in which the electron acceptor is diaphorase.

5. The method of claim 1 in which the aqueous solution additionally contains a myokinase inhibiting amount of AMP.

6. The method of claim 1 in which the aqueous solution additionally contains a CPK activating amount of a sulfhydryl compound.

7. The method of claim 6 in which the sulfhydryl compound is dithiothreitol.

8. The method of claim 1 in which the pH is maintained by a buffer selected from the group consisting of tris buffer and glycine and the electron acceptor is phenazine methosulfate.

* * * * *